United States Patent
Wimberger-Friedl et al.

(10) Patent No.: US 9,840,735 B2
(45) Date of Patent: Dec. 12, 2017

(54) BARRIER COATED NANO STRUCTURES

(71) Applicant: KONINKLIJKE PHILIPS N.V., Eindhoven (NL)

(72) Inventors: Reinhold Wimberger-Friedl, Veldhoven (NL); Christianne Rossette Maria De Witz, Lommel (BE); Cornelius Antonius Van Den Heuvel, Biest-Houtakker (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 14 days.

(21) Appl. No.: 14/410,114

(22) PCT Filed: Jun. 25, 2013

(86) PCT No.: PCT/IB2013/055214
§ 371 (c)(1),
(2) Date: Dec. 22, 2014

(87) PCT Pub. No.: WO2014/006540
PCT Pub. Date: Jan. 9, 2014

(65) Prior Publication Data
US 2015/0322505 A1 Nov. 12, 2015

Related U.S. Application Data

(60) Provisional application No. 61/666,963, filed on Jul. 2, 2012.

(51) Int. Cl.
C12Q 1/68 (2006.01)
G01N 21/64 (2006.01)
B82Y 15/00 (2011.01)
C23C 16/455 (2006.01)

(52) U.S. Cl.
CPC ...... *C12Q 1/6869* (2013.01); *C23C 16/45555* (2013.01); *G01N 21/648* (2013.01); *B82Y 15/00* (2013.01)

(58) Field of Classification Search
None
See application file for complete search history.

(56) References Cited

U.S. PATENT DOCUMENTS

| | | |
|---|---|---|
| 7,929,133 B2 | 4/2011 | Wang et al. |
| 8,070,928 B2 | 12/2011 | Sundberg et al. |
| 2007/0153267 A1 | 7/2007 | Wang et al. |
| 2010/0252751 A1 | 10/2010 | Klunder et al. |
| 2010/0284001 A1 | 11/2010 | Moskovits et al. |
| 2010/0303722 A1 | 12/2010 | Jin et al. |
| 2011/0081655 A1 | 4/2011 | Narahara et al. |

OTHER PUBLICATIONS

Tang et al., "Effects of interfacial oxide layers of the electrode metals on the electrical characteristics of organic thin-film transistors with HfO2 gate dielectric," J. Appl. Phys. 2011, 110:044108, published online Aug. 24, 2011.*
Choi et al., "Resistive switching mechanism of TiO2 thin films grown by atomic-layer deposition," J. Appl. Phys. 2005, 98:033715.*
Rezania et al., "Bioactivation of Metal Oxide Surfaces. 1. Surface Characterization and Cell Response," Langmuir 1999, 15:6931-6939.*
Yang et al., "Metallic Nanohole Arrays on Fluoropolymer Substrates as Small Label-Free Real-Time Bioprobes," Nano Lett. 2008, 8:2718-2724.*
Chafer-Pericas, C., et al.; Functionalized inorganic nanoparticles used as labels in solid-phase immunoassays; Trends in Analytical Chemistry; 31:144-156. 2012;.
Guo, D. J., et al.; GaN Nanowire Functionalized with Atomic Layer Deposition Techniques for Enhanced Immobilization of Biomolecules; 2010; Langmuir; 26(23)18382-18391.
Hausmann, D. M., et al.; Atomic Layer Deposition of Hafnium and Zirconium Oxides Using Metal Amide Precursors; 2002; Chem. Mater.; 14:4350-4358.
Im, H., et al.; Atomic Layer Deposition of Dielectric Overlayers for Enhancing the Optical Properties and chemical Stability of Plasmonic Nanoholes; 2010; ACS Nano; 4(2)947-954.
Kang, L., et al.; Highly Reliable Thin Hafnium Oxide Gate Dielectric; 1999; MRS Proceedings; 592.
Kim, H., et al.; Atomic Layer Deposition of Ultrathin Metal-Oxide Films for Nano-Scale Device Applications; 2006; Journal of the Korean Physical Society; 48(1)5-17.
Kukli, K., et al.; Atomic Layer Deposition of Hafnium Dioxide Films from Hafnium Tetrakis (ethylmethylamide) and Water; 2002; Chem. Vap. Deposition; 8(5)199-204.
Liu, R., et al.; Materials and Physical Properties of Novel High-k and Medium-k Gate Dielectrics; 2001; Mater. Res. Soc. Symp. Proc.; 670:K1.1.1-13.
Liu, X., et al.; ALD of Hafnium Oxide Thin Films from Tetrakis (ethylmethylamino)hafnium and Ozone; 2005; Journal of the Electrochemical Society; 152(3)G213-G219.

\* cited by examiner

*Primary Examiner* — Kaijiang Zhang

(57) ABSTRACT

A device includes a nano-structure made of electrically conductive material. The nano-structure is covered by a barrier coating comprising Ti, Zr, Hf, Nb, Ta, Mo, Sc, Y, Ge, La, Ce, Pr, Nd, Sm, Eu, Gd, Dy, Ho, Er, Tm, Yb, Lu, Sr, Al, B, Ba, Bi, and/or Mg oxide in a thickness of at least about 1 nm. The barrier coating is deposited by atomic layer deposition (ALD). A method of detecting a target compound uses the device for surface specifically creating an evanescent field, measuring the dielectric properties of a medium, detecting the presence or the concentration of a target compound, determining the primary structure of a target compound, determining a deviation of the target compound from a control value, amplifying a target compound, or monitoring the amplification of a target compound.

18 Claims, 6 Drawing Sheets

FIGURE 4

| Substrate | Chamber | Liquid | Top layer | Time to stability |
|---|---|---|---|---|
| Al wiregrid | Biograce | 5x SSC + 0.1% SDS | 5 nm SiO2 | 45-60 min |
| Al wiregrid | Biograce | 5x SSC + 0.1% SDS | 5 nm Si3N4 | 2.5-3.0 h |
| Al wiregrid | Biograce | 5x SSC + 0.1% SDS | 5 nm SiON4 + 5 nm SiO2 | ~3.5 h |
| Al wiregrid | Biograce | 5x SSC + 0.1% SDS | 10 nm TiN | ~3.5 h |
| Al wiregrid | Biograce | 5x SSC + 0.1% SDS | 5 nm SiO2 | 45-60 min |
| Al wiregrid | Home made chamber | 5x SSC + 0.1% SDS | 5 nm SiO2 | ~3.5 h |
| Al wiregrid | MF chamber | 5x SSC + 0.1% SDS | 5 nm SiO2 | >2.5 h | ced as WO 2014/006540 A1 on Jan. 9, 2014, which claims
BARRIER COATED NANO STRUCTURES

CROSS REFERENCE TO RELATED APPLICATIONS

This application is a national filing of PCT application Serial No. PCT/IB2013/055214, filed Jun. 25, 2013, published as WO 2014/006540 A1 on Jan. 9, 2014, which claims the benefit of U.S. provisional application Ser. No. 61/666, 963 filed Jul. 2, 2012, which is incorporated herein by reference.

FIELD OF THE INVENTION

The present invention relates to a device comprising a nano-structure, wherein said nano-structure is made of electrically conductive material and wherein said nano-structure is covered by a barrier coating comprising Ti, Zr, Hf, Nb, Ta, Mo, Sc, Y, Ge, La, Ce, Pr, Nd, Sm, Eu, Gd, Dy, Ho, Er, Tm, Yb, Lu, Sr, Al, B, Ba, Bi, and/or Mg oxide in a thickness of at least about 1 nm, wherein said barrier coating is deposited by atomic layer deposition (ALD). The present invention also relates to a method of detecting a target compound in such a device, the use of such a device for surface specifically creating an evanescent field, measuring the dielectric properties of a medium, detecting the presence or the concentration of a target compound, determining the primary structure of a target compound, determining a deviation of the target compound from a control value, amplifying a target compound, or monitoring the amplification of a target compound. Furthermore, the invention relates to a method of manufacturing a device comprising a nano-structure allowing for surface specific detection by creation of an evanescent field or for dielectric sensing comprising the deposition of a Ti, Zr, Hf, Nb, Ta, Mo, Sc, Y, Ge, La, Ce, Pr, Nd, Sm, Eu, Gd, Dy, Ho, Er, Tm, Yb, Lu, Sr, Al, B, Ba, Bi, and/or Mg oxide barrier coating in a thickness of at least about 1 nm on a electrically conductive material such as Al by atomic layer deposition (ALD).

BACKGROUND OF THE INVENTION

Fluorescence detection in biological and diagnostic devices is the most frequently used technique to measure and quantify the presence of biological entities, like proteins, nucleic acids and cells, in a sample. Generally this is done by selectively binding the target entities to a substrate surface by specific capture molecules. The targets may, for example, be labeled by a fluorescent molecule and the presence of the target is identified by measuring fluorescence on the surface against a background of fluorescence from the surrounding, e.g. bulk fluid, bulk substrate, etc. Depending on the analytical challenge this detection must be achieved at high spatial resolution and with high sensitivity, even down to single molecule level and over a large surface area. Real time observation requires surface selective detection. Nano-photonic structures comprising waveguides or apertures allow such surface specific detection by creation of an evanescent field between the structures, made of a electrically conductive material. They therefore constitute an advancement of fluorescence based detection, which is currently in biological and diagnostic devices the most frequently used technique to measure and quantify the presence of biological entities.

Typically, such nano-structures which need to have a high aspect ratio are made of aluminium, since anisotropic etching of Al allows the fabrication of high aspect ratio features at economic conditions. Alternative materials include gold and other electrically conductive materials.

Unfortunately, many biological reactions and assays require specific buffer systems comprising, inter alia, high salt concentrations or other chemicals which tend to react with the surface of the nano-structures and lead to their degradation. In particular, aluminium surfaces are rather vulnerable at high pH. Due to the small size of the nano-structures of below 1 μm and the tendency of the preferred material to degenerate in required environments, there is a need for an effective protection of the nano-structures. According to US 2010/0252751 dielectric material such as $SiO_2$ or $Si_3N_4$, which is applied isotropically, can be used as barrier coating material for nano-structures. The coating material needs to be conformal, i.e. has to protect the nano-structure from all sides and should lead to a pinhole free coverage. At the same time the coating should not be too thick in order to allow for access of the target molecules to the evanescence field. Si-based coatings as described in US 2010/0252751 were, however, found to provide no protection against buffer corrosion at the required thinness.

In consequence, there is a need for the development of an improved nano-structure barrier coating, which provides efficient protection against buffer corrosion during bioassays and allows for proficient evanescence field imaging.

OBJECTS AND SUMMARY OF THE INVENTION

The present invention addresses these needs and provides devices comprising barrier coated nano-structures, uses thereof as well as methods for their production. The above objective is in particular accomplished by a device comprising a nano-structure, wherein said nano-structure is made of an electrically conductive material and wherein said nano-structure is covered by a barrier coating comprising Ti, Zr, Hf, Nb, Ta, Mo, Sc, Y, Ge, La, Ce, Pr, Nd, Sm, Eu, Gd, Dy, Ho, Er, Tm, Yb, Lu, Sr, Al, B, Ba, Bi, and/or Mg oxide in a thickness of at least about 1 nm, and wherein said barrier coating is deposited by atomic layer deposition (ALD). In particular, it was found that hitherto described barrier coatings which are thin enough to benefit from an evanescent field for surface specific detection of nano-structures do not protect well enough in thicknesses below 20 nm. This behavior is speculated to be due to pin holes in the coating and/or other imperfections in these layers. In consequence, after exposure of correspondingly coated nano-structures, the exposure of the nano-structure to buffer solutions, e.g. sodium citrate buffers, leads to a degradation of the nano-structure. If, on the other hand, Ti, Zr, Hf, Nb, Ta, Mo, Sc, Y, Ge, La, Ce, Pr, Nd, Sm, Eu, Gd, Dy, Ho, Er, Tm, Yb, Lu, Sr, or W oxide, in particular Hf oxide, is deposited by atomic layer deposition onto the nano-structures in a thickness of about 1 nm or thicker, which allows for an efficient evanescence field imaging, the nano-structure may be exposed to several high salt buffers without loss of function. It was especially found that an optimal thickness of about 2 nm of an $HfO_2$ coating allowed to obtain the highest signal and highest signal to background ratio from a nano-structure comprising device. This finding allows to use such barrier coated nano-structures as nano-photonic structures for surface specific detection by creation of an evanescent field, or to use such barrier coated nano-structures or a plurality of these nano-structures as electrodes for measuring the dielectric properties of a medium surrounding a device. Thus, the presently provided approach effectively combines the advantages of evanescence field imaging and nano-scale electrode detection with the plethora of possibilities connected with bioassays or buffer based reaction assays.

In a preferred embodiment the device according to the present invention comprises electrically conductive material which is Al. In addition or in the alternative, the barrier coating preferably comprises Hf oxide.

In a further preferred embodiment of the present invention, a device as defined herein above is suitable for bioassays. In addition or alternatively, said structure covered by a barrier coating is preferably resistant to degradation by a liquid ionic, salt and/or detergent solution, such as a buffer solution.

In a further preferred embodiment, the present invention relates to a device as mentioned herein above, wherein said nano-structure covered by a barrier coating comprises a chemical function allowing for chemical coupling to biomolecules. In a particularly preferred embodiment, said chemical function is derived from a reaction with a bi-functional organo-silane. In a further preferred embodiment said chemical function is an aldehyde function, a primary amine function, a secondary amine function, a carboxy function or an epoxide function. In a further, optional embodiment said nano-structure is coupled to a biomolecule.

In yet another preferred embodiment of the present invention, said nano-structure as mentioned herein above is a nano-photonic structure and a device comprising said nano-photonic structure allows for surface specific detection by creation of an evanescent field in the apertures of said nano-photonic structure.

In another preferred embodiment of the present invention, said nano-photonic structure covered by a barrier coating forms, constitutes, comprises, or forms part of a wiregrid, of a plurality of wires, of a plurality of fibers, or of a mesh or plurality of meshes, or of any combination thereof. In addition, said nano-photonic structure preferably has feature sizes below the optical resolution of light.

In a particularly preferred embodiment of the present invention, a device as mentioned herein above comprises nano-scale apertures with dimensions of less than the optical resolution of light in at least one direction.

In another preferred embodiment of the present invention, said nano-structure or a plurality of said nano-structures forms, constitutes, comprises, or forms part of an electrode for measuring the dielectric properties of a medium surrounding said nano-structure or plurality of nano-structures.

In particularly preferred embodiments of the present invention, the device is a sequencing device, a fluorescence detector, or a microarray for the detection of nucleic acids or proteins.

In a further aspect, the present invention relates to a method of detecting a target compound in a device as mentioned herein above, comprising the steps of:

(a) emitting a beam or radiation having a wavelength incident at said device, preferably through the carrier;

(b) providing, by said device, evanescent radiation, in response to the radiation incident at said device; and (c) detecting emitted radiation from said target compound present in said device in response to said incident radiation.

In another aspect, the present invention relates to a method of detecting a target compound in a device as mentioned herein above, comprising the steps of:

(a) applying an alternating electrical field of a defined amplitude and frequency to a nano-electrode of said device; and (b) detecting amplitude and/or frequency changes in response to the presence and/or amount of a target compound in said device.

In yet another aspect the present invention relates to the use of a device as mentioned herein above for (i) surface specifically creating an evanescent field, (ii) measuring the dielectric properties of a medium, (iii) detecting the presence or the concentration of a target compound, (iv) for determining the primary structure of a target compound, (v) for determining a deviation of the target compound from a control value, (vi) for amplifying a target compound, or (vii) for monitoring the amplification of a target compound.

In a preferred embodiment of said method or use as mentioned herein above, said target compound is a molecule such as a nucleic molecule, e.g. a DNA molecule, an RNA molecule, an oligomeric nucleic acid molecule, or a nucleotide, a protein, a peptide, an amino acid, a sugar, a lipid, or an ion.

In a particularly preferred embodiment of the present invention, said method or use as mentioned herein above comprises the determination of a nucleic acid sequence, the determination of gene mutation or mRNA expression, or multiplexed, quantitative polymerase chain reaction (q-PCR).

Finally, in a further aspect, the present invention relates to a method of manufacturing a device comprising a nano-structure allowing for surface specific detection by creation of an evanescent field or for dielectric sensing, wherein said nano-structure is made of electrically conductive material and wherein said nano-structure is covered by a barrier coating comprising Ti, Zr, Hf, Nb, Ta, Mo, Sc, Y, Ge, La, Ce, Pr, Nd, Sm, Eu, Gd, Dy, Ho, Er, Tm, Yb, Lu, Sr, Al, B, Ba, Bi, and/or Mg oxide, the device being suitable for bioassays;

comprising the deposition of a Ti, Zr, Hf, Nb, Ta, Mo, Sc, Y, Ge, La, Ce, Pr, Nd, Sm, Eu, Gd, Dy, Ho, Er, Tm, Yb, Lu, Sr, Al, B, Ba, Bi, and/or Mg oxide barrier coating in a thickness of at least about 1 nm on a electrically conductive material such as Al by atomic layer deposition (ALD). In particularly preferred embodiments, the method comprises or optionally comprises the addition of one or more chemical functions allowing for chemical coupling to biomolecules, preferably by carrying out a reaction with a bi-functional organo-silane, more preferably by adding an aldehyde function, a primary amine function, a secondary amine function, a carboxy function, or an epoxide function. In yet another particularly preferred embodiment, said method further comprises or optionally further comprises the coupling of said chemical functions with one or more biomolecules.

BRIEF DESCRIPTION OF THE DRAWINGS

FIG. 4 shows results of experiments with alternative coating materials. As can be seen, all barrier coatings referred to as cover layer lead to degradation or etching.

DETAILED DESCRIPTION OF THE EMBODIMENTS

Figure 1:
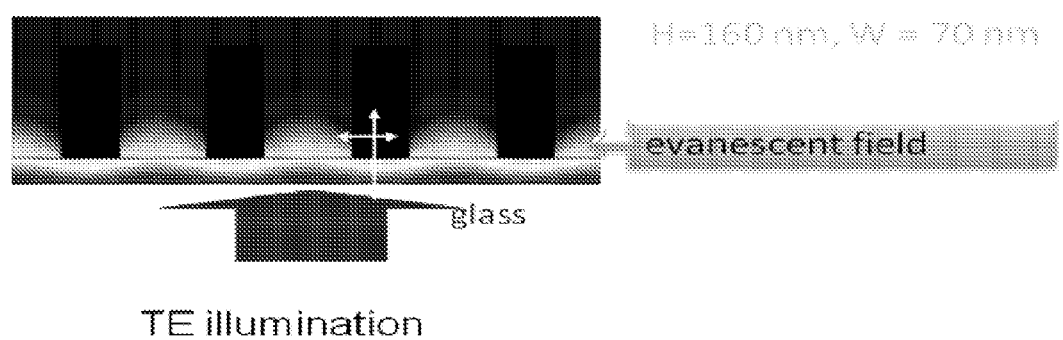
FIG. 1 shows a principle setup for an evanescence field imaging or evanescent field detection.

The present invention relates to a device comprising a nano-structure, wherein said nano-structure is made of electrically conductive material and wherein said nano-structure is covered by a barrier coating comprising Ti, Zr, Hf, Nb, Ta, Mo, Sc, Y, Ge, La, Ce, Pr, Nd, Sm, Eu, Gd, Dy, Ho, Er, Tm, Yb, Lu, Sr, Al, B, Ba, Bi, and/or Mg oxide in a thickness of at least about 1 nm.

Although the present invention will be described with respect to particular embodiments, this description is not to be construed in a limiting sense.

Before describing in detail exemplary embodiments of the present invention, definitions important for understanding the present invention are given.

As used in this specification and in the appended claims, the singular forms of "a" and "an" also include the respective plurals unless the context clearly dictates otherwise.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)", "i", "ii" etc. relate to steps of a method or use or assay there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

It is to be understood that this invention is not limited to the particular methodology, protocols, reagents etc. described herein as these may vary. It is also to be understood that the terminology used herein is for the purpose of describing particular embodiments only, and is not intended to limit the scope of the present invention that will be limited only by the appended claims. Unless defined otherwise, all technical and scientific terms used herein have the same meanings as commonly understood by one of ordinary skill in the art.

As has been set out above, the present invention concerns in one aspect a device comprising a nano-structure, wherein said nano-structure is made of electrically conductive material and wherein said nano-structure is covered by a barrier coating comprising Ti, Zr, Hf, Nb, Ta, Mo, Sc, Y, Ge, La, Ce, Pr, Nd, Sm, Eu, Gd, Dy, Ho, Er, Tm, Yb, Lu, Sr, Al, B, Ba, Bi, and/or Mg oxide in a thickness of at least about 1 nm, wherein said barrier coating is deposited by atomic layer deposition (ALD).

The term "device" as used herein refers to a structure, e.g. a receptacle, chamber or container, or an instrument, or part of an instrument, or a part of a system, which allows or is suitable for the performance of reactions, in particular molecular reactions involving chemical and/or biological entities. The device may correspondingly be equipped, for example, with one or more inlet and/or outlet elements, it may comprise one or more surfaces, e.g. reactive surfaces or surfaces with specific functionality, it may comprise a reaction zone, a washing zone, a mixing zones, a waiting zone, a measurement zone, a waste zone, a reservoir zone, a recollection or a regeneration zone etc. or any sub-portion or combination thereof. It may further comprise connections between these elements, e.g. tubes or joints; and/or it may comprise reservoirs and repositories for liquids, fluids, chemicals, ingredients, samples or any other entity to be used within the device. Preferably, it may comprise a reaction zone wherein said reaction zone comprises a nano-structure or a plurality of nano-structures. Such a "reaction zone" may be a closed entity comprising only inlet and/or outlet structures being of a minor size in comparison to the size of the zone and be understood as a "reaction chamber", or it may be an open structure being in free or semi-free connection with further entities present in a device or a system. The reaction zone may be suitable for allowing molecular reactions involving chemical and/or biological entities, or may, in certain embodiments, be equipped with or comprise elements allowing a reaction to take place in said entity. To be suitable for allowing a reaction one or more parameters may be set or adjusted in a reaction zone. For example, the temperature in a reaction zone may be adjusted to a suitable value known to the person skilled in the art. The value may largely depend on any target compound or entity to be selected and the reaction or interaction type taking place and may differ in dependence of the reactant type, the reaction category, the envisaged speed, reaction end point considerations and further parameters known to the person skilled in the art. Elements allowing a reaction to take place may be substrates, arrays of chemical, biochemical, biological or other entities, catalyst etc. Furthermore, a reaction zone may be composed of regions suited for measurement or movement activities, e.g. it may comprise a moveable surface allowing for a reduction of the enclosed space, and/or it may comprise electrically conductive zones or capacitor zones etc. and/or it may comprise one or more transparent surfaces allowing an optical detection. In certain embodiments the dimension and/or form of the reaction may be adapted to one of the above indicated functions. In a further embodiment the device may additionally or alternatively comprise one or more detection zones. This zone may be identical to the other zones, in particular the reaction zone, or it may be separated from the other zones, e.g. the reaction zone or the mixing zone etc. The detection zone may comprise detector elements, e.g. for electrically and/or optically detecting reaction products, reaction results or for checking whether reaction steps have been concluded or not. These zones may comprise, for example, electrically conductive zones or capacitor zones etc. or they may comprise one or more transparent surfaces allowing an optical detection, e.g. of reaction results such as, for example, the performance or intensities of labeling reaction etc. For example, said detection zone may comprises a nano-structure or a plurality of nano-structures as described herein.

In further embodiments of the invention the device may additionally or alternatively comprise heating modules or regulating units for controlling and/or regulating the temperature, e.g. a heating zone wherein the temperature may be kept constant at a desired value, or may be set to a desired value in dependence of a reaction type or reaction cycle etc. In further embodiments the device may additionally or alternatively comprise cooling modules, e.g. a cooling zone wherein the temperature may be kept constant at a desired value, or may be set to a desired value in dependence of a reaction type or reaction cycle etc. These zones may further also be equipped with suitable sensor elements allowing the measurement of temperature changes or temperature gradients.

Additionally or alternatively, the device may comprise units, elements or equipment allowing to change further parameters such as the presence of charged entities, the presence of ions, or may convey mechanical or shearing forces etc. For example, the element(s) may be suited to establish an electric or electrophoretic current, the element(s) may be suited to provide a specific pH or a specific presence of chemical or physical entities, e.g. the presence of certain acids, salts, ions, solvents etc. and/or the element(s) may be suited to provide a strong medium movement. Any of the above mentioned additional facilities may be available in any part of a device, e.g. in a reaction zone or reaction chamber.

In further specific embodiments the device may additionally or alternatively comprise modules allowing the detection of flow velocity, viscosity or density values, the transition of one state to another, the presence or absence of reagents etc.

In further embodiments, the device may be provided on a carrier or carrier structure. Such a carrier may, for example, consist of, comprise or essentially comprise glass or plastic material. Suitable plastic material would be, for example, polystyrene or polycarbonate. In certain embodiments of the present invention, it is preferred that the carrier material is transparent, e.g. comprising transparent glass or plastic material. The carrier material may further be present, or constitute units of the device as mentioned above, e.g. wall structures, tubes or joints etc.

The term "nano-structure" as used herein refers to a 3 dimensional structure in the nanometer scale, e.g. having in each direction a dimension of about 0.5 nm to about 100 nm being present in or on said device, or constituting one or more zones of said device, e.g. a reaction zone or detection zone. In specific embodiments, a nano-structure may have in one or two directions a dimension of 0.5 nm to about 100 nm, and in the third direction a dimension in the μm or mm range, e.g. about 1 μm to about 1 mm, 10 mm, 50 mm or more mm. The structure may comprise any suitable 3 dimensional form. It may be a linear form, an angled or bent form, a curved form, a round form or any combination or mixture thereof. The structure may preferably constitute strips or walls in linear or bent form. The structure may further constitute a fissure or aperture in a flat layer. The structure may, in further embodiments, comprise one or more circular, elliptic or rectangular openings, gaps or pockets. The structure may, in further embodiments, be in parallel to a layer or carrier, or may be inclined in one, two or three directions or axes regarding a layer or carrier. The nano-structure may be provided in a periodic manner, e.g. comprising repetitive units in one, two or three directions or axes. Alternatively, the nano-structure may be provided in an aperiodic or quasi-periodic manner, e.g. comprising repetitions with increasing or decreasing dimensions or distances. The nano-structure may, in further embodiments, be provided in a single layer on a carrier or ground layer, or it may be provided in a multiple layer form. Multiple layers may comprise layers with identical nano-structures in off-set or shifted. Multiple layers may, in alternative embodiments, comprise layers with essentially different nano-structures.

The term "electrically conductive material" as used herein refers to material which contains movable electric charges. Examples of such material, which are envisaged by the present invention, are copper (Cu), gold (Au), silver (Ag), chromium (Cr), Platinum (Pt), Nickel (Ni), Palladium (Pd) and aluminium (Al). It is preferred that the nano-structure consists of, comprises or essentially comprises aluminium (Al).

The nano-structure of electrically conductive material may be covered by a barrier coating. The term "barrier coating" refers to a coating or superficial layer, which covers the nano-structure or plurality of nano-structures on or in a device, e.g. all nano-structures or the plurality of nano-structures present on a device are covered by a barrier coating. The coverage of the nano-structure or plurality of nano-structures in or on a device may be complete or essentially complete. It is preferred that the barrier coating be equally spread on all accessible parts of the nano-structures. In specific embodiments, the coating may be spread essentially equally, or it may not be spread entirely equally on all parts of the nano-structures and/or on all nano-structures present on or in a device. For example, nano-structures being located at the termini of the device may be coated with less or with more barrier coating. Furthermore, certain sections of the nano-structure may be coated with less barrier coating than other sections, certain sections of the nano-structure may be coated with more barrier coating than other sections. For example, protruding sections of nano-structures may be covered with more barrier coating, than caved-in sections. In further specific embodiments, the device may comprise sections which are entirely void of barrier coating. These sections may be predetermined or specifically designed. The coverage of the nano-structures as well as the uniformity of said coverage may be determined and/or adjusted by the method used for providing said coating. In further embodiments the barrier coating may comprise a single uniform layer. In other embodiments, the barrier coating may be comprised of multiple layers. These layers may be identical, essentially identical or be different. Different layers may comprise, for example, different materials, may have different physical and/or chemical properties, may have different thicknesses, and/or may have been provided with different methodologies or deposition processes etc. Multiple layers may further comprise repetitions of layer combinations, for example a repetition of layer 1 plus layer 2, or a repetition of layer 1 plus layer 2 plus layer 3. These layer combinations may, for example, be present 1, 2, 3, 4, 5, 6, 7, 8, 9, 10 times or more times.

The barrier coating may comprise, essentially comprise or consist of a suitable dielectric material. Preferably, the barrier coating comprises a dielectric material which can be applied by a suitable method to the nano-structure. More preferably, the barrier coating may comprise, essentially comprise or consist of a dielectric material which can be applied by atomic layer deposition (ALD). Examples of barrier coating material include Ti oxide, Zr oxide, Hf oxide, Nb oxide, Ta oxide, Mo oxide, Sc oxide, Y oxide, Ge oxide, La oxide, Ce oxide, Pr oxide, Nd oxide, Sm oxide, Eu oxide, Gd oxide, Dy oxide, Ho oxide, Er oxide, Tm oxide, Yb oxide, Lu oxide, Sr oxide, Al oxide, B oxide, Ba oxide, Bi oxide and Mg oxide, or any combination thereof. Preferred oxides include $Al_2O_3$, $TiO_2$, $ZrO_2$, $HfO_2$, $Ta_2O_5$, $Nb_2O_5$, $Sc_2O_3$, $Y_2O_3$, MgO, $B_2O_3$, $GeO_2$, $La_2O_3$, $CeO_2$, $PrO_x$, $Nd_2O_3$, $Sm_2O_3$, $EuO_x$, $Gd_2O_3$, $Dy_2O_3$, $Ho_2O_3$, $Er_2O3$, $Tm_2O_3$, $Yb_2O_3$, $Lu_2O_3$, $SrTiO_3$, $BaTiO_3$, $PbTiO_3$, $PbZrO_3$, $Bi_xTi_yO$, $SrTa_2O_6$, $SrBi_2Ta_2O_9$, $YScO_3$, $LaAlO_3$, $NdAlO_3$, $GdScO_3$, $LaScO_3$, $LaLuO_3$, $Er_3Ga_5O_{13}$ or any combination thereof. In further specific embodiments of the present invention, the barrier coating material may comprise, essentially comprise or consist of $In_2O_3$, $In_2O_3$:Sn, $In_2O_3$:F, $In_2O_3$:Zr, $SnO_2$, $SnO_2$:Sb, ZnO, ZnO:Al, ZnO:B, ZnO:Ga, $RuO_2$, $RhO_2$, $IrO_2$, $Ga_2O_3$, $V_2O_5$, $WO_3$, $W_2O_3$, NiO, $FeO_x$, $CrO_x$, $CoO_x$, $MnO_x$, $LaCoO_3$, $LaNiO_3$, $LaMnO_3$, $La_{1-x}Ca_x$-$MnO_3$. In further embodiments, the barrier coating may comprise, essentially comprise or consist of suitable nitrides. Examples of suitable nitrides are BN, AlN, GaN, InN, $Ta_3N_5$, $Cu_3N$, $Zr_3N_4$, $Hf_3N_4$, Ti—Al—N, TaN, NbN, MoN, $WN_x$, and $WN_xC_y$. The present invention further envisages any combination of the above mentioned oxides and nitrides. In a particularly preferred embodiment, the barrier coating material may comprise, essentially comprise or consist of Hf oxide, more preferably of $HfO_2$. In further embodiments, the barrier coating may comprise one layer of a specific material, e.g. oxide or nitride as mentioned above, followed by a layer of a different material, e.g. oxide or nitride as defined above etc. Multilayer barrier coatings may, however, also be composed of the same type of material as defined herein above, e.g. Hf oxide, preferably $HfO_2$.

The barrier coating may have a thickness of at least about 1 nm. The thickness of the barrier coating may be, for example, in a range of about 1 nm to about 20 nm, more preferably, in a range of about 1 nm to about 12 nm, more preferably in a range of about 1 nm to about 10 nm. In specific embodiments of the invention the thickness of the barrier coating may be about 1 nm, 1.5 nm, 2 nm, 2.5 nm, 3 nm, 3.5 nm, 4 nm, 4.5 nm, 5 nm, 5.5 nm, 6 nm, 6.5 nm, 7 nm, 7.5 nm, 8 nm, 8.5 nm, 9 nm, 9.5 nm, 10 nm, 10.5 nm, 11 nm, 11.5 nm, 12 nm, 12.5 nm, 13 nm, 13.5 nm, 14 nm, 14.5 nm, 15 nm, 15.5 nm, 16 nm, 16.5 nm, 17 nm, 17.5 nm, 18 nm, 18.5 nm, 19 nm, 19.5 nm, 20 nm or more, or any value in between the indicated values. The thickness of the barrier coating may be adjusted in dependence of the barrier coating material, the intended use of the device, the nature of the conductive material and other suitable factors as known to the person skilled in the art. The barrier coating may, in certain situations, have a thickness which differs in specific sectors of the device comprising electrically conductive material. For example, the device may comprise on one side a barrier coating with a thickness of about 10 nm and on the other side a barrier coating with a thickness of about 2 nm, or vice versa. The device may, in further embodiments also comprise a thickness gradient (low to high, or high to low) parallel to at least one direction or axis of the device. The thickness differences may further follow the form, presence and density of the nano-structures. In other embodiments, the barrier thickness as indicated above may be equal or essentially equal in all sectors comprising electrically conductive material. In a particularly preferred embodiment of the present invention, the thickness of the barrier coating is about 2 nm or 2 nm.

The barrier coating is further to be deposited by atomic layer deposition (ALD). The "atomic layer deposition" method is a thin film deposition technique that is based on the sequential use of a gas phase chemical process. The process is typically self-limiting, i.e. the amount of film material deposited in each reaction cycle is constant, and the sequential surface chemistry deposits conformal thin-films of barrier coating material as defined herein onto nano-structures of electrically conductive material as mentioned herein above. The ALD process may comprise, for example, the following steps, which can be repeated several times: (a) exposure of a first precursor, (b) evacuation of the reaction chamber to remove non-reacted precursors and gaseous reaction by-products, (c) exposure of a second precursor or treatment to active surfaces and (d) evacuation of reaction chamber. During each cycle of the process a certain amount of barrier coating material may be added to the nano-structure. The reaction cycles may be repeated as often as necessary in order to arrive at a desired thickness, e.g. a thickness as mentioned herein above. Further details and application modes would be known to the skilled person and can be derived from suitable literature sources such as Liu et al., 2005, Journal of The Electrochemical Society, 152 (3), G213-G219. In a preferred embodiment, the ALD process leads to a conformal and essentially uniformly thick coating of the nano-structure or plurality of nano-structures according to the present invention.

In a particularly preferred embodiment of the present invention the device comprises a nano-structure as defined herein above, which comprises, essentially comprises or consists of Al. In a further particularly preferred embodiment of the present invention the device comprises nano-structures covered by Hf oxide, preferably $HfO_2$, in a thickness of at least 1 nm, which has been deposited by atomic layer deposition. In yet another particularly preferred embodiment of the present invention, the device comprises a nano-structure as defined herein above, which comprises, essentially comprises or consists of Al and said nano-structures are covered by Hf oxide, preferably $HfO_2$, in a thickness of at least 1 nm, which has been deposited by atomic layer deposition.

In a preferred embodiment, the device as defined herein above is suitable for bioassays. The term "suitable for bioassays" means that in said device or with said device a bioassay may be carried out such that typical or expected assay results can be obtained. This suitability includes the possibility to fully and successfully employ the coated nano-structures in environments of bioassays such as aqueous environments, aqueous environments comprising buffer chemicals, salts, ions, detergents, biological material, cells, cell debris, nucleotides, sugars, peptides, proteins, etc. In further specific embodiments, this suitability includes the non-toxicity of the coated nano-structures for biological entities such as cells or sub-cellular fragments. In yet further specific embodiments, this suitability includes a non-inhibitory or non-degrading effect on chemical or biological entities, e.g. on enzymes, proteins, peptides, nucleic acids, e.g. RNA or DNA, cells, sub-cellular fragments such as organelles etc.

In a further preferred embodiment, the coated nano-structure or plurality of nano-structures as defined herein above is resistant to degradation by an environments of bioassays, e.g. by an aqueous environment. In particular, the coated nano-structure may be resistant to an aqueous environment comprising buffer chemicals, salts, ions, detergents, biological material, cells, cell debris, nucleotides, sugars, peptides, proteins, etc. In further embodiments, the coated nano-structure or plurality of nano-structures as defined herein above is resistant to liquid ionic, salt and/or detergent solution. In a particularly preferred embodiment, the coated nano-structure or plurality of nano-structures as defined herein above is resistant to a buffer solution. Examples of buffer solutions to which the nano-structure or plurality of nano-structures as defined herein above is resistant include sodium citrate buffers, e.g. 1×, 5×, 10×SSC buffer etc., or buffers comprising SDS, e.g. 0.1% SDS, 0.5% SDS. The term "resistant to degradation" as used herein means that the barrier coating of the nano-structure protects the nano-structure, e.g. the Al metal, against chemical attacks or reactions by chemical entities in the surrounding medium or corresponding environmental effects, e.g. by buffer components, salts or ions etc. This protection may be a permanent protection or a transitional protection. A "transitional protection" as used herein refers to a protection against degradation over a time period of about 10 to 500 h of contact with an environment or medium as mentioned herein above. For example the transitional protection may be a protection over a time period of 10 h, 11 h, 12 h, 13 h, 14 h, 15 h, 16 h, 17 h, 18 h, 19 h, 20 h, 21 h, 22 h, 23 h, 24 h, 25 h, 30 h, 40 h, 50 h, 70 h, 100 h, 150 h, 200 h, 250 h, 300 h, 400 h, 500 h or more than 500 h or any value in between the indicated time period. The protection may depend on the bioassay carried out, the amount of salts, ions, detergents etc. used, the temperature applied during the assay and other factors known to the skilled person, leading to an reduction or prolongation of the above indicated protection period.

In a further embodiment of the present invention the nano-structure covered by a barrier coating as defined herein above comprises a chemical function which allows for chemical coupling to secondary molecules. The term "chemical function which allows for chemical coupling" as used herein refers to any entity or residue accessible or being present in the outer layer of said barrier coating, which is able to react with a secondary molecule. Examples of such entities or residues are OH-groups. Further examples are organic functional groups such as aldehydes, primary amines, secondary amines, carboxy groups or epoxides. These entities may either be already present in the barrier coating, e.g. OH-groups, or they may be attached therewith, preferably indirectly attached therewith, after the deposition process, e.g. aldehydes, primary amines, secondary amines, carboxy groups or epoxides. Suitable methods for chemical coupling would be known to the skilled person, and can be derived from a suitable literature source such as Mittal et al., Silanes and other coupling agents, Vol. 2 to 5, 2001-2009, Brill Academic Pub. In a particularly preferred embodiment of the present invention, a chemical coupling may be initiated by a reaction with a bifunctional organo-silane. Examples of suitable organo-silanes include organo-silanes with reactive groups such as methoxy, ethoxy or Cl functions. These bifunctional organo-silanes may preferably react with chemical groups already present on the surface of a barrier coating, in particular with OH-groups. In addition, said bifunctional organo-silanes may comprise one or more secondary organic functional groups. Examples of such secondary functional groups are aldehydes, primary amines, secondary amines, carboxy groups or epoxides. These secondary functional groups thus may allow for a coupling with secondary molecules, e.g. biomolecules. In particular embodiments of the present invention suitable bifunctional organo-silanes may be silanes comprising methoxy functionality and an aldehyde function, silanes comprising methoxy functionality and a primary amine function, silanes comprising methoxy functionality and a secondary amine function, silanes comprising methoxy functionality and an epoxide function, silanes comprising methoxy functionality and a carboxy function, silanes comprising ethoxy functionality and an aldehyde function, silanes comprising ethoxy functionality and a primary amine function, silanes comprising ethoxy functionality and a secondary amine function, silanes comprising ethoxy functionality and an epoxide function, silanes comprising ethoxy functionality and a carboxy function, silanes comprising Cl functionality and an aldehyde function, silanes comprising Cl functionality and a primary amine function, silanes comprising Cl functionality and a secondary amine function, silanes comprising Cl functionality and an epoxide function, or silanes comprising Cl functionality and a carboxy function. A device as defined herein above may comprise coated nano-structures comprising such chemical functions at specific sections or in specific positions. For example top-most positions or low positions of nano-structures may show such chemical functions. Furthermore, the chemical functions may be provided in a certain regularity, e.g. every 2, 3, 4, 5, 6, 7, 8, 9, 10 nm or more, or on every or every second etc. wall structure or aperture etc. Furthermore, the nano-structure may be equipped with such chemical functions only in the center portion of the device, or only in one or more corners of a rectangular setup, or in a central circle or square of the device etc.

In particular embodiments, the chemical functions which allow for chemical coupling can be used for the coupling of a biomolecule. Examples of such biomolecules are an antibody, a nucleic acid or a nucleotide, e.g. a DNA molecule or an RNA molecule, a protein, e.g. a lectin, an enzyme, such as a DNA-polymerase, or an RNA-polymerase, a peptide, or an amino-acid. Furthermore, organic molecules such as small molecules or any type of binding molecule, e.g. organic binding molecules or protein binding molecules may be coupled to the device according to the present invention. Particularly preferred is the coupling of antibodies or antibody fragments or derivatives. The term "antibody" as used herein refers to immunoglobulin molecules and immunologically active portions of immunoglobulin molecules, i.e. molecules that contain an antigen binding site that immunospecifically binds an antigen. The immunoglobulin molecules of the invention can be of any type (e. g., IgG, IgE, IgM, IgD, IgA and IgY), class (e. g., IgG1, IgG2, IgG3, lgG4, lgA1 and IgA2) or subclass of immunoglobulin molecule. The antibody may be a polyclonal, monoclonal, multispecific, human, humanized or chimeric antibody, a single chain antibody, Fab fragment, Fab' fragment, fragment produced by a Fab expression library, F(ab')2, Fv, disulfide linked Fv, minibody, diabody, scFv, sc(Fv)2, whole immunoglobulin molecule, binding-domain immunoglobulin fusion proteins, camelized antibody, $V_{HH}$ containing antibody, or anti-idiotypic (anti-Id) antibody. The antibody may be from any animal origin preferably a human, murine (e. g., mouse and rat), donkey, monkey, rabbit, goat, guinea pig, camel, horse, or chicken antibody. The antibody may further be monospecific, bispecific, trispecific or of greater multispecificity. Also particularly preferred is the binding of oligomeric single stranded DNA, e.g. DNA of a length of about 20 to about 60 nucleotides. The oligomeric nucleic acids may be selected according to their complementarity to nucleic acids intended to be detected. Further examples include poly-T oligomeres, allowing to detect mRNA or cDNA species comprising polyA stretches.

The biomolecules as mentioned above can be linked to said coupling entities via any suitable reaction schemes. For example, a bifunctional organo-silane as mentioned above may be coupled to DNA molecules, e.g. poly-T oligonucleotides. Typical deposition techniques include inkjet printing of said oligonucleotides on the surface. Subsequently, the biomolecule may be fixed, e.g. by applying UV radiation, resulting in a crosslinking reaction. Further suitable coupling or immobilization approaches for biomolecules which are also envisaged by the present invention are carboxyl to amine coupling such as EDC or EDC-HHS coupling, amine reactive coupling such as NHS ester or imidoester based coupling, sulfhydryl-reactive coupling, e.g. maleimid, haloacetyl or pyridyldisulfide based coupling, carbonyl-reactive coupling such as hydrazine or alkoxyamine based coupling, photoreactive coupling based on aryl azides or diazirines, or chemosensitive ligation based on Staudinger reagent pairs. In further specific embodiments, nucleic acid molecules may also be provided by in situ synthesis approaches, e.g. synthesis approaches as marketed by Affymetrix.

In a further, optional embodiment a nano-structure as defined herein above, in particular a nano-structure activated by a bifunctional organo-silane as described herein, is coupled to a biomolecule as mentioned herein. The present invention thus specifically envisages devices comprising chemical functions which allow for chemical coupling, as well as devices and nano-structures comprising thereby coupled biomolecules as mentioned herein, e.g. a device comprising one or more coupled antibodies, one or more coupled nucleic acid molecules, one or more coupled proteins or enzymes etc. Coupled biomolecules such as antibodies may be provided in essentially identical forms, e.g. comprising only one antibody, only one antibody type, or antibodies binding to only one antigen or one epitope. In further embodiments, different biomolecules may be coupled at the same time to one or more nano-structures covered by a barrier coating of one device or of one zone of a device or a system comprising said device, e.g. two or more different antibodies, polymerases, e.g. DNA-polymerases, two or more different polymerases, e.g. DNA-polymerases, two or more different antibody types, two or more antibodies which bind to different antigens or epitops, or mixtures of nucleic acids and proteins, or nucleic acids and antibodies etc.

In a particularly preferred embodiment said nano-structure is a nano-photonic structure and the device allows for surface specific detection by creation of an evanescent field in the apertures of said nano-photonic structure. The term "nano-photonic structure" as used herein refers to a structure which can control the flow of light or radiation and may localize or confine it within a volume. The term "allows for surface specific detection by creation of an evanescent field in the apertures of said nano-photonic structure" as used herein means that the nano-photonic structure is a structure which allows evanescence field imaging and thereby detection of molecular adsorption of molecules to a surface wherein the adsorbing molecules cause changes in the local index of refraction and thereby modify the resonance conditions of the evanescence waves. In order to be capable of conveying this effect the apertures of the nano-structures have to be adapted to specific parameters. In a typical embodiment, the aperture defining nano-structures may have a first smallest in plane aperture dimension which is smaller than a diffraction limit, wherein the diffraction limit ($W_{min}$) is defined by the surrounding medium, e.g. a medium comprising target compounds. According to $$W_{min} = \lambda/(2 \cdot n_{medium})$$

with $\lambda$ the wavelength in vacuum and n medium the refractive index of the environment medium in front of the nano-structures the diffraction limit may be calculated. The wavelengths may typically vary in visible ranges of 400 to 800 nm, which corresponds to a minimum aperture of about 150 to 300 nm in water or an aqueous solution. The nano-photonic structure as defined herein above may accordingly define a first and a second in-plane vector that is parallel to structures of electrically conductive material on the device as defined herein above. According to specific embodiments of the present invention correspondingly obtainable apertures are:

(1) Apertures of a first-type with a first in-plane dimension below the diffraction limit and a second in-plane dimension above the diffraction limit, wherein a transmission plane that is composed of the first in-plane vector and a third vector that is normal to the first and second in-plane vectors. In this configuration R-polarized incident light, that is light having an electric field orthogonal to the plane of transmission, may be substantially reflected by the aperture defining structure and may generate an evanescent field inside the aperture. T-polarized light incident on an aperture defining structure composed of apertures of the first type, that is light having an electric field parallel to the planes of transmission of the one or more apertures, may be substantially transmitted by the aperture defining structure and may generates a propagating field inside the aperture.

(2) Apertures of a second-type include those with both in-plane dimensions below the diffraction limit which does not allow the definition of a plane of transmission. Incident light of any polarization (such as linearly, circularly, elliptically, randomly polarized) may be substantially reflected by the aperture defining structure and may generate an evanescent field inside the aperture.

A device which allows for surface specific detection by creation of an evanescent field in the apertures of nano-photonic structure according to the present invention may, in specific embodiments, comprise the following components:

(1) A carrier with a binding surface at which target compounds can collect. The device may, in specific embodiments, also define a detection volume without a binding surface. The term "binding surface" refers to a particular part of the surface of the carrier. The target compound may, alternatively, also bind to different sections of the device. The target compounds may accordingly reach the binding surface to collect there (typically in concentrations determined by parameters associated to the target components, to their interaction with the binding surface, to their mobility etc.). In preferred embodiments, the carrier may be produced from glass or transparent plastic. The carrier may further be permeable and provides a carrying function for aperture defining structures as defined herein above. The carrier may accordingly fulfill the function of a prism thus contributing to the generation of an evanescent field. Alternatively, a carrier structure may be present which allows an evanescent field be generated by suitable objectives or lens systems and parallel input beams. In further embodiments, a carrier structure may be provided in the form and implementing an optical waveguide comprising a transparent substrate and a transparent core layer.

(2) A source for emitting an "incident light beam", i.e. a beam of radiation, into the mentioned carrier such that it is reflected, at least in an investigation region at the binding surface of the carrier. The light source may for example be a laser or a light emitting diode (LED), optionally provided with some optics for shaping and directing the incident light beam. The "investigation region" may be a sub-region of the binding surface or comprise the complete binding surface; it will typically have the shape of a substantially circular spot that is illuminated by the incident light beam.

(3) A detector for detecting radiation from the target compound present in the detection volume, in response to the emitted incident radiation from the source. The term "radiation from the target compound" includes any radiation that is detectable for detecting a presence of the target compound. For example, the radiation may be of a scattered, reflected or luminescent type. The detector may comprise any suitable sensor or plurality of sensors by which light of a given spectrum can be detected, for example a photodiode, a photo resistor, a photocell, or a photo multiplier tube. The term "light" or "radiation" as used herein relates to all types of electromagnetic radiation, in particular, depending on context, as well visible as non visible electromagnetic radiation.

(4) Near the binding surface an optical element or region comprising one or a plurality of nano-photonic structures as defined herein above is positioned. The nano-photonic structures may generate evanescent radiation, in response to the radiation incident at the binding surface, in a detection volume bound by the binding surface and extending over a decay length away from the binding surface into, for example, a sample chamber. The optical element or region is preferably provided such that the evanescent field substantially does not propagate after said optical region, i.e. an out of plane dimension of the aperture defining structure may be substantially larger than the 1/e decay length.

The device may further comprise optical filtering systems, e.g. for scattering light or reflected excitation light, or focusing lenses which can be actuated for scanning a surface and for adaptive focusing. Furthermore, the device may be connected to image detection and computerized data storage systems etc.

The term "evanescent radiation" in a given medium as used herein refers to non-propagating waves having a spatial frequency that is larger than the wave-number of a given medium (i.e. the wave-number in vacuum times the refractive index of the medium). Examples of evanescent radiation are evanescent waves generated by total internal reflection or by incidence on a sub-diffraction limited apertures. In particular, the evanescent wave-field will typically decay with a 1/e decay length of about 10-500 nm depending on the illumination light.

The term "target compound" as used herein refers to any compound which can be detected or measured with the help of a device according to the present invention or according to the methodology of the present invention. The target compound may be a chemical entity, e.g. an organic or inorganic compound such as a small molecule, a ion, etc., or a biomolecule or biological or biochemical entity. Examples of such biomolecules include a nucleic molecule, e.g. a DNA molecule, an RNA molecule, an oligomeric nucleic acid molecule, a nucleotide, a protein, a peptide, an amino acid, a sugar, a lipid. In specific embodiments, the target compound may also be a cell, a cellular fragment, a subcellular unit, a membrane or membrane portion. The target compound may be provided in a suitable sample, e.g. a buffer solution, an aqueous solution with a specific pH, a specific ion concentration etc. These sample solutions may be adapted to the target compounds included and may comprise additional elements such as RNAse inhibitors, proteinase inhibitors etc.

In further typical embodiments of the present invention, the target compound may be prepared for analysis or measurement processes with a device according to the present invention. This preparation typically includes the labeling of the target compounds with suitable labels. This can in principle be accomplished by using any labels, which can be conjugated to a detection molecule, using suitable technique or methods known to the person skilled in the art. Such labels may be fluorescent, chromophoric, electroluminescent or chemiluminescent labels. Examples of labels include fluorescent dyes such as fluorescein, rhodamine, phycoerythrin, or fluorescamine, chromophoric dyes such as e.g. rhodopsin, chemiluminescent compounds such as luminal, or imidazole and bioluminescent proteins such as luciferin, luciferase, green fluorescent protein, yellow fluorescent protein, and derivatives thereof. Further examples of fluorescent labels are 6-FAM, HEX, TET, ROX, Cy3, Cy5, Cy7, Texas Red, Alexa, or Atto dyes. In further embodiments of the invention secondary labels may be used, e.g. for detection of hybridization. Such secondary labels may include intercalators, e.g. mono- or bis-intercalating dyes, cyanine intercalator dyes, fluorogenic intercalating dyes, or benzothioxanthene dyes, or molecular beacons which fluoresce upon hybridization, e.g. comprising a fluorophore and a quencher. Examples of suitable quenching label are TAMRA, Dabcyl, Black Hole Quencher, BHQ-1 or BHQ-2.

In yet another embodiment of the present invention, the target compound may be linked to a quantum dot or a quantum dot agent.

A variety of other useful fluorescents and chromophores are known to the person skilled in the art and can be derived from suitable literature sources.

In a further, particularly preferred embodiment said nano-photonic structure covered by a barrier coating forms, constitutes, comprises, or forms part of a wiregrid, of a plurality of wires, of a plurality of fibers, or of a mesh or plurality of meshes, or of any combination thereof. The term "wiregrid" as used herein relates to metallic wires which are placed in certain embodiments in a plane perpendicular to an incident beam. In other embodiments one axis of the wiregrid may be perpendicular to a beam such as a focused beam. In yet further embodiments, beams may further have an oblique incidence with regard to the axis of wires of a wiregrid. The wiregrid may, for example, comprise strips, walls, wires or a grate of coated electrically conductive material which provides evanescent radiation. The aperture of this grid is preferably such that the feature sizes are below the optical resolution of light. The term "feature size" as used herein refers to the diffraction limit W min of the smallest in plane aperture as mentioned herein above. Further, alternative forms such as fibers, or meshes may be provided essentially on the basis of the architecture of a wiregrid as mentioned above. A mesh may, for example, combine more than one wiregrid in a two or more layer setup. Fibers may be provided in periodic, a-periodic or quasi periodic conformation. Further conformations, e.g. asymmetric conformations etc. are also possible as long as the generation of evanescent radiation according to the above mentioned rationales is possible. In specific embodiments, strips or fibers as mentioned herein may preferably be about 50 to 2000 nm thick, more preferably about 50 to 150 nm. In further embodiments, the spacing between adjacent strips or fibers may be about 25 to 100 nm. In preferred embodiments evanescent decay lengths in between wires or fibers of about 10 to 50 nm may be obtained. The strip or fiber dimensions may, in corresponding embodiments, be chosen or adapted such that evanescent decay lengths in the range of 25 to 75 nm are obtained. Further details would be known to the person skilled in the art.

In a particularly preferred embodiment a device according to the present invention comprises nano-scale apertures with dimensions of less than the optical resolution of light in at least one dimension. For example, a device may have nano-scale apertures with a first in-plane dimension below the diffraction limit for incident radiation, and a second in-plane dimension having a dimension above the diffraction limit for incident radiation. One of these dimensions may be an x axis or an y axis of an essentially rectangular structure. In a preferred embodiment, said at least one dimension may be 250 nm or smaller, more preferably 50 nm or smaller.

The present invention further relates to a device, wherein said nano-structure or a plurality of said nano-structures as defined herein above forms, constitutes, comprises, or forms part of an electrode. The nano-structure electrode may be connected by signal paths or electric conductive coupling to downstream elements, e.g. one or more voltage sources, one or more switches, which are preferably implemented as transistors, e.g. CMSO switch transistors, or control circuits. The device may further be equipped with readout units or electronics, computer units. A device according to the present invention may comprise a single nano-structure electrode, or more than one nano-structure electrode, e.g. 2, 10, 100, 1000, 10000, 100000, 1000000, 10000000, 100000000 or any value in between these values, or more than 100000000 electrodes. In case a plurality of nano-structure electrodes is present, the electrodes may be provided in the form of an array. The array may have a rectangular, hexagonal, circular or ellipsoid shape, or be formed in strips or triangles etc. The array may further comprise additional barrier material to separate single nano-structure electrodes. A nano-structure electrode according to the present invention works such that the barrier coating as defined herein above, e.g. a Ti, Zr, Hf, Nb, Ta, Mo, Sc, Y, Ge, La, Ce, Pr, Nd, Sm, Eu, Gd, Dy, Ho, Er, Tm, Yb, Lu, Sr, Al, B, Ba, Bi, or Mg oxide, preferably a Hf oxide, is provided on the surface of the electrode as dielectric layer.

According to specific embodiments of the present invention, said coating of an electrode has a preferred thickness of at least about 1 nm. The thickness of the barrier coating of the electrode may be, for example, in a range of about 1 nm to about 20 nm, more preferably, in a range of about 1 nm to about 12 nm, more preferably in a range of about 1 nm to about 10 nm. In specific embodiments of the invention the thickness of the barrier coating may be about 1 nm, 1.5 nm, 2 nm, 2.5 nm, 3 nm, 3.5 nm, 4 nm, 4.5 nm, 5 nm, 5.5 nm, 6 nm, 6.5 nm, 7 nm, 7.5 nm, 8 nm, 8.5 nm, 9 nm, 9.5 nm, 10 nm, 10.5 nm, 11 nm, 11.5 nm, 12 nm, 12.5 nm, 13 nm, 13.5 nm, 14 nm, 14.5 nm, 15 nm, 15.5 nm, 16 nm, 16.5 nm, 17 nm, 17.5 nm, 18 nm, 18.5 nm, 19 nm, 19.5 nm, 20 nm or more, or any value in between the indicated values. The thickness of the barrier coating of the electrode may be adjusted in dependence of the barrier coating material, the intended use of the electrode, the nature of the conductive material and other suitable factors as known to the person skilled in the art. The barrier coating may, in certain situations, have a thickness which differs in specific sectors of the device comprising electrically conductive material. In further embodiments, an electrode according to the present invention may have a thickness of about 10 nm to about 1000 nm, e.g. a thickness of about 20 nm, 50 nm, 100 nm, 200 nm, 300 nm, 400 nm, 500 nm, 600 nm, 700 nm, 800 nm, 900 nm, 1000 nm, or any value in between. Further, a thickness of the electrode of more than 1000 nm is also envisaged.

In specific embodiments, the device comprising nano-structure electrodes may be built of wiregrids, strips or fibers as mentioned herein, e.g. strips and fibers 50 to 2000 nm thick, more preferably strips and fibers having sizes of about 50 to 150 nm. In other embodiments, the strips and fibers may be 10 to 50 nm thick. In further embodiments, the spacing between adjacent strips or fibers may be about 25 to 100 nm. The strip or fiber dimensions may, in specific corresponding embodiments, be chosen or adapted such that evanescent decay lengths in the range of 25 to 75 nm are obtained. In further specific embodiments, devices comprising nano-structure electrodes may have a setup, configuration, dimension and/or form as defined for nano-photonic devices herein above or below.

Essentially, the electrode or plurality of electrodes covered by said dielectric layer thus forms part of a capacitor, whose counter side is constituted by the volume of the surrounding medium. Thereby, the device allows for measuring of dielectric properties of medium surrounding said nano-structure electrode or plurality of nano-structures electrodes. The term "measuring dielectric properties" as used herein refers to the detection of charged entities, e.g. charged molecules or ions, or the detection of electric fields generated by charged entities. This measuring may, for example, be carried out by applying an electrical field, e.g. an alternating electrical field, to a nano-structure electrode, thus allowing for detection of amplitude or frequency changes in response to the presence of charged entities. The measurement may preferably be carried out based on principles of ISFET, dielectric spectroscopy or impedance spectroscopy. Further details are known to the skilled person and can be derived from suitable literature sources such as Kremer et al., Broadband Dielectric Spectroscopy, Springer, 2002.

In specific embodiments of the present invention, said nano-structure electrode or plurality of nano-structure electrode may be coupled, e.g. by the coupling chemistry as mentioned herein, to a biomolecule. Examples of such biomolecules are an antibody, a nucleic acid or a nucleotide, e.g. a DNA molecule or an RNA molecule, a protein, an enzyme, a peptide, or an amino-acid. The coupling to an antibody or to a nucleic acid, as mentioned herein above, is preferred. For example, single stranded DNA oligomeric capture probes may be coupled to said nano-structure electrodes, thus allowing for detection of changes in the electrical field upon the hybridization of complementary nucleic acids. Similarly, binding proteins such as antibodies or antibody variants as mentioned herein above may be used for detecting interaction with their ligands via detection of changes in the electrical field. In further embodiments of the present invention, a polymerase or a plurality of polymerases, e.g. DNA-polymerase or RNA-polymerase may be coupled to one or more nano-structure electrodes. In yet another embodiment, nucleic acid molecules and enzymes such as polymerases may be coupled to the same nano-structure electrode or neighbouring nano-structure electrodes, thus allowing for an interaction between the enzyme, e.g. polymerase and the nucleic acid. Due to the resistance of the barrier coating towards buffer ingredients, or ions etc., an efficient electrochemical detection becomes possible. The nano-structure electrodes may, in specific embodiments, form cavities, holes or pits, which allow the performance of bioassays, e.g. an interaction of enzymes and nucleic acids, the detection of ion concentration changes etc. A device may accordingly comprise an amount of several such cavities, holes or pits, e.g. 10, 100, 1000, 10000 or 100000, 1000000, 10000000, 100000000 or any value in between these values, or more than 100000000. In further specific embodiments, such cavities, hole or pits may constitute nano-photonic structures as defined herein above, allowing for the generation of evanescent fields and the detection of correspondingly emitted radiation from a target compound present in said cavity, hole or pit in response to an incident radiation as described herein. In a specific embodiment of the present invention, said nano-structure electrode or plurality of nano-structure electrodes, or said cavity, hole or pit according to the present invention as defined above is not associated, equipped or linked with a bead or particle or other external structural element having a size of about 200 nm or more, in particular a size of 0.2 µm, 0.3 µm, 0.7 µm, 1 µm, 1.05 µm, 2.5 µm or 5.9 µm, e.g. a bead comprising one or more biomolecules or target compounds such as nucleic acids, DNA, RNA or enzymes such as polymerases.

In further embodiments, a device according to the present invention may comprise a nano-structure electrode or plurality of nano-structures electrodes as defined above and one or more nano-photonic structure covered by a barrier coating as defined above. The device may, for example, comprise an integrated version of nano-electrodes and nano-photonic structures, allowing for surface specific detection by creation of an evanescent field and for dielectric sensing. The device may also comprise both elements, nano-electrodes and nano-photonic structure at confined sections, which may be non-overlapping, or partially overlapping. In yet another envisaged embodiment, a device according to the present invention may comprise a nano-structure electrode or plurality of nano-structures electrodes which at the same time works as or is a nano-photonic structure covered by a barrier coating as defined above.

In a particularly preferred embodiment of the present invention, the device as defined herein above is a sequencing device, a fluorescence detector, a microarray for the detection of nucleic acids, a microarray for the detection of proteins. The device may further be an ionosensor, a pH sensor, a screening device for interaction of small molecules or binding interactions. The device may be used as such, or it may be integrated in a system, e.g. a row of similar devices, an integrated setup comprising, for example, control and readout units, automatized preparation, storage or cleaning facilities, connection units allowing the backup of data, or the access to the system from remote sites, e.g. over internet or intranet etc. A sequencing device may, for example, be implemented on the basis of a device comprising nano-photonic structures as described herein, which allow the optical detection of complementary binding, e.g. coupled nucleic acids. Alternatively, a sequencing device may be implemented on the basis of a device comprising nano-structure electrodes as described herein, which allow the electric detection of complementary binding, e.g. coupled nucleic acids. In a further alternative embodiment, a sequencing device may be implemented on the basis of a device comprising nano-photonic structures as described herein and comprising nano-structure electrodes as described herein, allowing for the electric detection of complementary binding, e.g. coupled nucleic acids and the optical detection of complementary binding, e.g. coupled nucleic acids. A fluorescence detector may preferably be implemented on the basis of a device comprising nano-photonic structures as described herein, which allow the optical detection of binding of labeled molecules, e.g. fluorescently labeled molecules such as biomolecules or target compounds as defined herein, to the surface of the device creating evanescent radiation as described herein above. The fluorescent device may accordingly be equipped with suitable light or radiation sources such as lasers, as well as suitable detection units. In specific embodiments the device may be equipped with more than one light source and/or more than one wavelength detector allowing for the detection of fluorescence at different wavelengths, e.g. due to the employment of fluorescent labels with different excitation and emission wavelengths. A microarray for the detection of nucleic acids may preferably be implemented on the basis of a device comprising nano-photonic structures as described herein, which allow the optical detection of binding of labeled target compounds such as nucleic acids or nucleic acid binding proteins to a complementary nucleic acid among a plurality of immobilized single stranded nucleic acid molecules coupled to the nano-structures as defined herein. Said single stranded nucleic acid molecules may be oligomeric DNA molecules of a length of about 20 to about 60 bases. The plurality of immobilized nucleic acids may comprise portions of different genes of an organism, e.g. portions or stretches of all, essentially all, or a percentage of 90%, 80%, 70%, 60%, 50%, 40%, 30%, 20%, 10%, 5% or 2% of all genes or of all exons of an organism, or a of a population of organisms. The choice of immobilized nucleic acids may further include specific pathway members, population specific genes, metabolism related genes, genes known to be associated with certain diseases or a predisposition for diseases, SNP containing sectors of the genome, transposon landing sites etc. A microarray for the detection of proteins may preferably be implemented on the basis of a device comprising nano-photonic structures as described herein, which allow the optical detection of binding of labeled target compounds such as proteins, peptides, small organic molecules, antibodies or nucleic acids to an interacting protein or protein fragment among a plurality of immobilized interacting proteins or protein fragments coupled to the nano-structures as defined herein. The present invention also envisages further implementations of the device, e.g. as sensor for molecular diagnostics or clinical diagnostics, as part of a point-of care diagnostics sensor, as advanced bio-molecular diagnostic research-bio sensors. The device may further be implemented as environmental sensor, e.g. allowing the detection of toxic compounds or pollution indicators, or as food quality sensor, implementing the detection of toxic compounds, or food quality parameters.

In a further aspect the present invention relates to a method of detecting a target compound as defined herein above in a device comprising nano-photonic structures as described herein, comprising the steps of:

(a) emitting a beam or radiation having a wavelength incident at said device, preferably through the carrier;

(b) providing, by said device, evanescent radiation, in response to the radiation incident at said device; and (c) detecting emitted radiation from said target compound present in said device in response to said incident radiation.

A beam or radiation having a wavelength incident at the device may be emitted by suitable light sources such as a laser or a LED. The wavelength of the beam or radiation may vary in dependence of the aperture of the nano-structures, the surrounding medium etc. Typically, a wavelength in the range of 400 to 800 nm may be applied, e.g. a wavelength of about 650 nm. The carrier to be used may preferably be transparent, e.g. a glass or transparent plastic unit as defined herein above. The carrier may accordingly fulfill the function of a prism thus contributing to the generation of an evanescent field. Alternatively, an evanescent field may be generated by using a suitable objectives or lens systems and parallel input beams. In further embodiments, an evanescent field may be generated by an optical waveguide comprising a transparent substrate and a transparent core layer. The beam or radiation subsequently produces evanescent radiation, e.g. in the form of fluorescent radiation. Scattered light may preferably be blocked by using specific filters. The generation of evanescent radiation may be adjusted by the patterning of the nano-structures, their aperture, the identity and amount of labeled entities, the identity and amount of target compound, the wavelengths of the beams etc. Parameters such as the amount of labels and the wavelength of the beams may, for example, be changed continuously, or in dependence of the assays carried out. In a last step, the emitted radiation from the target compound present in the device is detected in response to the incident radiation. The detection may be carried out by suitable detector units, e.g. a pixilated light detector or a CCD camera. The detection may further be assisted by the use of focusing units, e.g. additional lenses. Detected radiation may subsequently be transferred to control or analysis units or data storage units, e.g. computerized image detection and interpretation systems.

In yet another aspect the present invention relates to a method of detecting a target compound as defined herein above in a device comprising nano-structure electrodes as described herein, comprising the steps of:

(a) applying an alternating electrical field of a defined amplitude and frequency to a nano-electrode of said device; and (b) detecting amplitude and/or frequency changes in response to the presence and/or amount of a target compound in said device.

The electrical field may be applied according to any suitable means, e.g. by using voltage sources as mentioned herein above. The amplitude and/or frequency of the field may be defined according to parameters of the device, the nano-structure electrode, the target compound to be detected, the amount of charges in the surrounding medium etc. Typically, an amplitude of about 0.5 to about 10 V, e.g. about 1 V, 2 V, 3V, 5 V, 7 V etc. and/or a frequency in the range of about 1 MHz to about 1-10 GHz may be used, e.g. about 10 MHz, 100 MHz, 1 GHz, 10 GHz etc. It is preferred that the amplitude and frequency are CMOS compatible. The field is further applied in alternating form, i.e. as alternating current, preferably in a sine wave form, or as rectangular pulse. Any changes to the amplitude or the frequency of the field may subsequently be detected by a suitable sensor, or electrical field detector, e.g. an antenna and receiver system. Detected alterations of the electrical field may subsequently be transferred to control or analysis units or data storage units, e.g. analysis, data mining and interpretation systems. The control of the electrodes may preferably by performed by semiconductor elements, in particular CMOS elements, or combinations of CMOS elements with sensor, detection, analysis or storage elements.

Devices or parts thereof, or systems comprising one or more of these devices as defined herein above may be used in a further aspect of the present invention for a variety of purposes. Specifically, such a device or a part thereof, or systems comprising one or more of these devices may be used for creating an evanescent field, which is surface specific. Accordingly, by using suitable emitting radiation an evanescent field may be generated which allows the detection of surface bound target compounds, e.g. biomolecules, via the emitted radiation of said target compounds, or the detection of the performance or outcome of molecular interactions or reactions involving target compounds on or near the surface of the device. A device or a part thereof, or systems comprising one or more of these devices may further be used for measuring dielectric properties of a medium, or volume. The measurement may in particular be carried out in a setup in which the properties of the medium are modified or changed, e.g. due to the presence or absence of target compounds etc. A device or a part thereof, or systems comprising one or more of these devices may additionally be used for detecting the presence or the concentration of a target compound. The presence of a target compound may be detected by detecting an amount of target compound which is below a threshold defined for the occupancy of interaction positions in a device as defined herein, e.g. about 0.5, 0.1 or 0.01% or less of all possible interaction positions are occupied. The amount or concentration of a target compound may be determined by the occupancy of interaction positions based on a known or predetermined number of these positions, or by comparing a measured value with one or preferably two control or calibration values for known amounts or concentrations of a target compound. The present invention also envisages, in specific embodiments, a corresponding method for detecting the presence or the concentration of a target compound. A device or a part thereof, or systems comprising one or more of these devices, may also be used for determining the primary structure of a target compound. The term "primary structure" as used herein refers to a structure which is determinable following a straight-forward chemical or biochemical analysis of a target compound, essentially excluding complex image determination approaches. Examples of such primary structures are the nucleotide sequence of a nucleic acid or the amino acid sequence of a protein. These primary structures exclude more complex information such as 3 dimensional conformation etc. The device according to the present invention may be used for such determination processes either via nano-structure electrodes or via nano-photonic structures as described herein, or via both, nano-structure electrodes and nano-photonic structures. The present invention also envisages, in specific embodiments, a corresponding method for determining the primary structure of a target compound. The present invention in particular envisages a corresponding method for determination of a nucleic acid sequence. A device or a part thereof, or systems comprising one or more of these devices may further be used for determining a deviation of the target compound from a control value. Such a use includes, for example, the determination of the sequence of a target compound, e.g. DNA, and a comparison of the sequence with a control sequence, e.g. derived from a database or determined in a different setup or a parallel device. It may also be the determination of the presence and/or amount of a protein in a collection of proteins, and the comparison of the result with control information on the amount or presence of said protein, e.g. derivable form a database or determined in a different setup or a parallel device. The present invention also envisages, in specific embodiments, a method for determining the deviation of the target compound from a control value, in particular for determining the sequence of a nucleic acid in comparison to a control or wildtype sequence. A device or a part thereof, or systems comprising one or more of these devices may also be used for amplifying a target compound or complementary parts thereof. Examples thereof are the amplification of nucleic acids, in particular DNA or RNA. DNA amplification may accordingly be based on principles of polymerase chain reaction (PCR). RNA amplification may be based on the Nucleic acid sequence based amplification (NASBA) technique. The present invention also envisages, in specific embodiments, a corresponding method for amplifying a target compound or complementary parts thereof. A device or a part thereof, or systems comprising one or more of these devices may further be used for monitoring the amplification of a target compound or complementary parts thereof. The "monitoring" may, for example, comprise the determination of the amount of amplified product, their concentration, the increase or decrease of amplified product over time etc. Typically, such an amplification is an amplification of nucleic acids, in particular DNA or RNA. The present invention also envisages, in specific embodiments, a corresponding method for monitoring the amplification of a target compound or complementary parts thereof.

Further specific examples of methods based on devices according to the present invention and of uses of a device or a part thereof, or systems comprising one or more of these devices according to the present invention include the determination of gene mutation or mRNA expression, the performance of multiplexed and/or quantitative polymerase chain reaction (q-PCR). Further envisaged uses include the use of a device or a part thereof, or systems comprising one or more of these devices according to the present invention, for determination of the presence of disease associated genetic or genomic information, or the detection of genes or genetic aberrations associated with certain diseases or a predisposition for diseases. Further uses include the detection of SNPs, the analysis of SNP containing sectors of the genome etc. Also envisaged is the use of a device or a part thereof, or of a system comprising one or more of these devices according to the present invention, for screening of small molecules, e.g. by performing binding studies to target entities. A device or a part thereof, or a system comprising one or more of these devices according to the present invention, may further advantageously be used as sensor for molecular diagnostics or clinical diagnostics, as part of a point-of care diagnostics sensor, or as bio-molecular diagnostic research-bio sensors. A device or a part thereof, or a system comprising one or more of these devices according to the present invention, may additionally be used for the detection of toxic compounds or pollution indicators, or as food quality sensor, e.g. for detecting of toxic compounds, or for determining one or more food quality parameters.

In a further aspect the present invention relates to a method of manufacturing a device comprising a nano-structure allowing for surface specific detection by creation of an evanescent field or for dielectric sensing as defined herein above. In a preferred embodiment, said nano-structure is made of electrically conductive material and said nano-structure is covered by a barrier coating comprising Ti, Zr, Hf, Nb, Ta, Mo Sc, Y, Ge, La, Ce, Pr, Nd, Sm, Eu, Gd, Dy, Ho, Er, Tm, Yb, Lu, Sr, and/or W oxide. In a further additional or alternative embodiment, said device is suitable for bioassays.

Preferably, said method comprises the deposition of a Ti, Zr, Hf, Nb, Ta, Mo Sc, Y, Ge, La, Ce, Pr, Nd, Sm, Eu, Gd, Dy, Ho, Er, Tm, Yb, Lu, Sr, and/or W oxide barrier coating in a thickness of at least about 1 nm on a electrically conductive material. The coating may, in certain embodiments also be deposited in a thickness of about 1 nm to about 20 nm, more preferably, in a range of about 1 nm to about 12 nm, more preferably in a range of about 1 nm to about 10 nm. In specific embodiments of the invention the thickness of the barrier coating may also be about 1 nm, 1.5 nm, 2 nm, 2.5 nm, 3 nm, 3.5 nm, 4 nm, 4.5 nm, 5 nm, 5.5 nm, 6 nm, 6.5 nm, 7 nm, 7.5 nm, 8 nm, 8.5 nm, 9 nm, 9.5 nm, 10 nm, 10.5 nm, 11 nm, 11.5 nm, 12 nm, 12.5 nm, 13 nm, 13.5 nm, 14 nm, 14.5 nm, 15 nm, 15.5 nm, 16 nm, 16.5 nm, 17 nm, 17.5 nm, 18 nm, 18.5 nm, 19 nm, 19.5 nm, 20 nm or more, or any value in between the indicated values. The thickness of the barrier coating may further be adjusted in dependence of the barrier coating material, the intended use of the device, the nature of the conductive material and other suitable factors as known to the person skilled in the art. The barrier coating may, in certain situations, have a thickness which differs in specific sectors of the device comprising electrically conductive material.

The electrically conductive material which is preferably used is Al. It is particularly preferred to use Hf oxide, e.g. $HfO_2$, for the generation of said barrier coating.

The deposition may be carried out by any suitable deposition technique. Preferred is atomic layer deposition (ALD). Further details and features of ALD, and how the deposition may be carried out are known to the skilled person and can, for example, be derived from Liu et al., 2005, Journal of The Electrochemical Society, 152 (3), G213-G219.

In further embodiments of the present invention, the manufacturing of a device as described herein above also comprises the addition of one or more chemical functions allowing for chemical coupling to biomolecules. Such a chemical coupling may be initiated by a reaction with a bifunctional organo-silane. Examples of suitable organo-silanes include organo-silanes with reactive groups such as methoxy, ethoxy or Cl functions. These bifunctional organo-silanes are preferably reacted with chemical groups already present on the surface of a barrier coating, in particular with OH-groups. In addition, said bifunctional organo-silanes comprise one or more secondary organic functional groups. Examples of such secondary functional groups are aldehydes, primary amines, secondary amines, carboxy groups or epoxides. These secondary functional groups thus may allow for a coupling with secondary molecules such as biomolecules. In specific embodiments of the present invention, said addition of chemical functions thus includes an addition of bifunctional molecules, preferably of bifunctional organo-silanes. Preferred examples of suitable bifunctional organo-silanes are silanes comprising methoxy, ethoxy or Cl functions. Further preferred examples of suitable bifunctional organo-silanes are silanes comprising methoxy functionality and an aldehyde function, silanes comprising methoxy functionality and a primary amine function, silanes comprising methoxy functionality and a secondary amine function, silanes comprising methoxy functionality and an epoxide function, silanes comprising methoxy functionality and a carboxy function, silanes comprising ethoxy functionality and an aldehyde function, silanes comprising ethoxy functionality and a primary amine function, silanes comprising ethoxy functionality and a secondary amine function, silanes comprising ethoxy functionality and an epoxide function, silanes comprising ethoxy functionality and a carboxy function, silanes comprising Cl functionality and an aldehyde function, silanes comprising Cl functionality and a primary amine function, silanes comprising Cl functionality and a secondary amine function, silanes comprising Cl functionality and an epoxide function, or silanes comprising Cl functionality and a carboxy function. The number and frequency of occurrence of these chemical functions may be adjusted, e.g. by increasing or decreasing the amount of reactions leading to the addition of these chemical functions. Furthermore, in specific embodiments, more than one chemical function type may be provided in a device, i.e. on a surface.

In particularly preferred embodiments, the manufacturing of a device as described herein additionally also includes the coupling of one or more of said chemical functions with one or more biomolecules. Preferred examples of a biomolecule to be coupled include an antibody, a nucleic acid or a nucleotide, e.g. a DNA molecule or an RNA molecule, a protein, e.g. a lectin, an enzyme, a peptide, or an amino-acid. Furthermore, organic molecules such as small molecules may be coupled, or any type of binding molecule, e.g. organic binding molecules or protein binding molecules.

The manufacturing may be carried out according to any suitable production schemes, for example in an automatized manner, e.g. by robotic production lines. Accordingly produced devices may further be integrated in larger systems or detection packs.

The present invention also envisages the production of parts of a device only, e.g. a sector comprising nano-structures as defined herein. The present invention further envisages the recycling or reequipping of previously used devices, e.g. the replacement or stockpiling of coupled biomolecules etc., the replacement of broken tubes etc., and/or the recoating of nano-structures.

The following examples and figures are provided for illustrative purposes. It is thus understood that the examples and figures are not to be construed as limiting. The skilled person in the art will clearly be able to envisage further modifications of the principles laid out herein.

EXAMPLES

Example 1—Degradation of Coating

Figure 2:
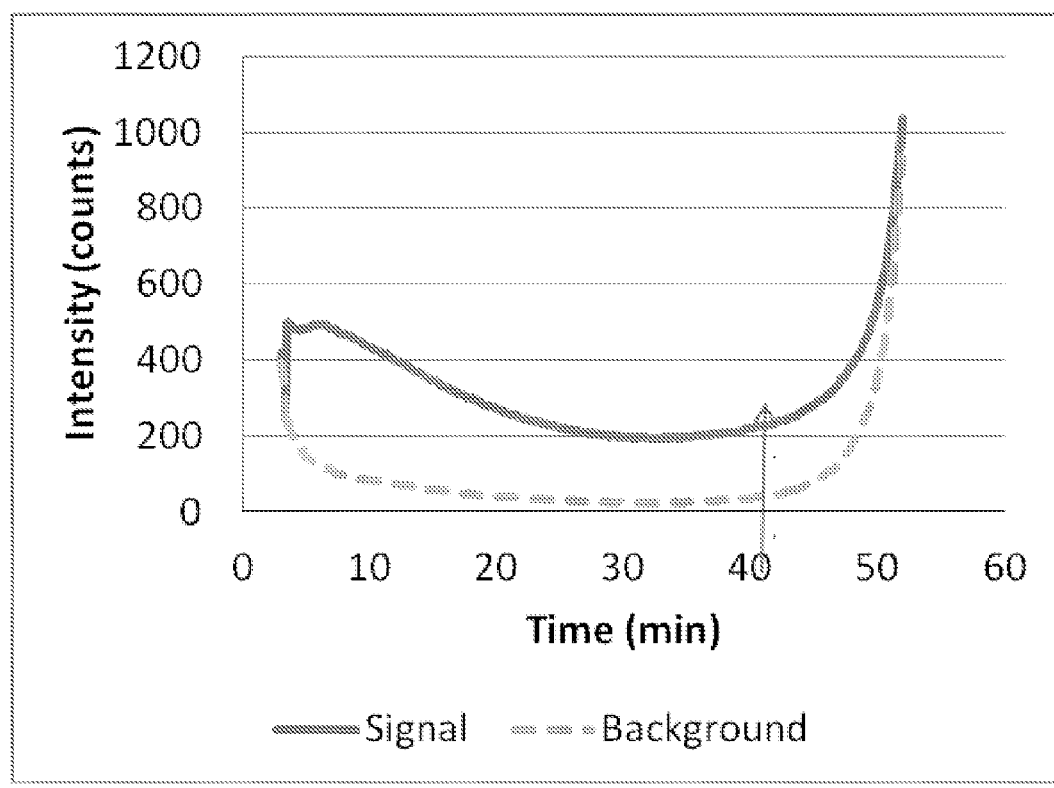
FIG. 2 shows the onset of aluminium degradation after app. 40 min in 5×SSC buffer. The wiregrid was coated with 5 nm silicon nitride.
Figure 3:
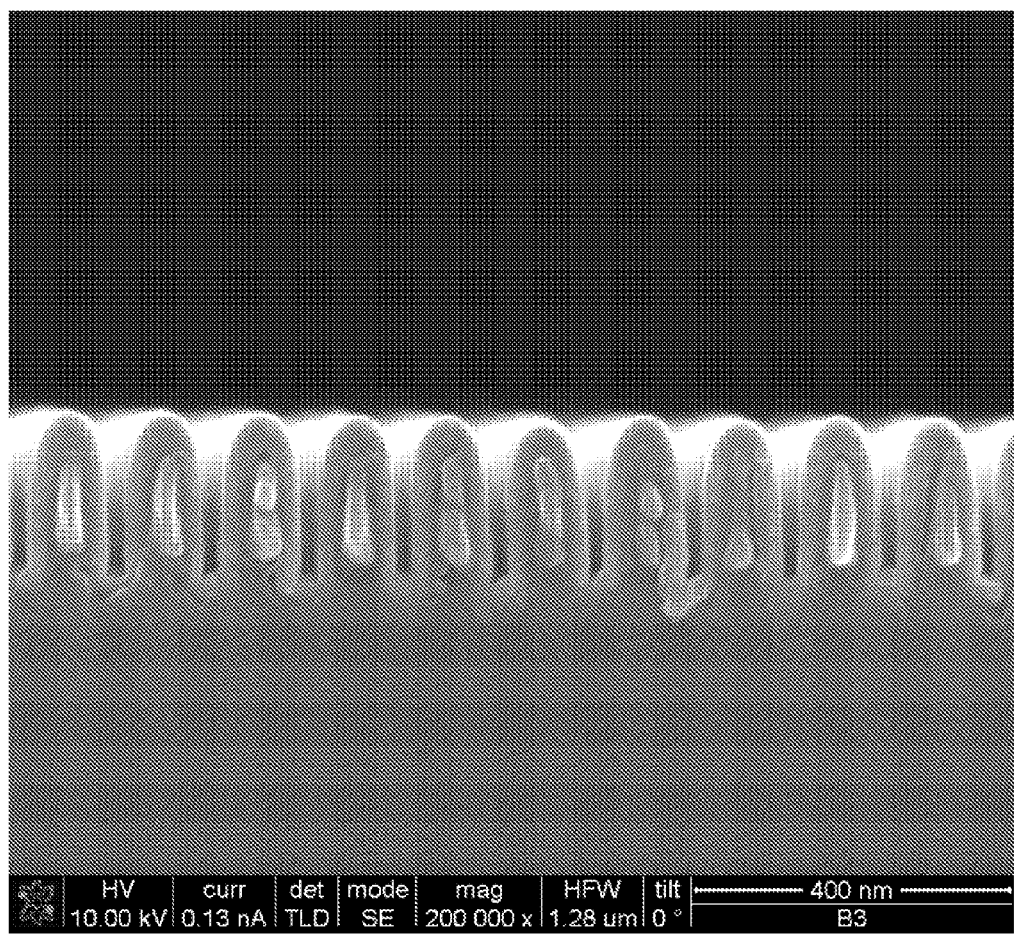
FIG. 3 demonstrates a SEM graph of a wiregrid with a thick barrier coating. As can be seen, the barrier coating reduces the gap for access of biomolecules between the grid lines and lifts the bottom out of the evanescent field. This leads to a drastic reduction in performance.

The degradation of coating material in typical bioassay buffers was tested in the following way: A wiregrid was coated with 5 nm silicon nitride and subsequently immersed in a 5×SSC buffer with 0.1% SDS at room temperature. The evanescent field signal intensity was measured during a time frame of 50 minutes. As can be derived from the graph of FIG. 2, the background signal increased due to the loss of metallic Al as a consequence of the reaction with the buffer. This lead to an increase of the decay length until light could pass through the nano-structure. The degradation onset was after app. 40 min (indicated by an arrow in FIG. 2).

Example 2—Experiments with Alternative Coating Materials

The degradation of different coating materials in typical bioassay buffers was tested in the following way: An Al wiregrid in a Biograce, a home-made and a microfluidic chamber were coated with 5 nm $SiO_2$, 5 nm $Si_3N_4$, 5 nm $SiON_4$+5 nm $SiO_2$, 10 nm TiN, and 5 nm $SiO_2$ and subsequently immersed in a 5×SSC buffer with 0.1% SDS at room temperature. The evanescent field signal intensity was measured during a time frame of up to 4 h. As can be derived from FIG. 4, the background signal increased due to the loss of metallic Al as a consequence of the reaction with the buffer. This lead to an increase of the decay length until light could pass through the nano-structure. The degradation onset is indicated in FIG. 4 for the different cover layers. The time to etching was found to be at 45-60 min for 5 nm $SiO_2$ in a Biograce chamber, 2.5-3 h for $Si_3N_4$ in a Biograce chamber, about 3.5 h for 5 nm $SiON_4$+5 nm $SiO_2$ in a Biograce chamber, about 3.5 h for 10 nm TiN in a Biograce chamber, 45-60 min for 5 nm $SiO_2$ in a Biograce chamber, about 3.5 h for 5 nm $SiO_2$ in a home-made chamber and more than 2.5 h for 5 nm $SiO_2$ in a micro fluidic chamber.

Example 3—Coating with $HfO_2$

Figure 5A:
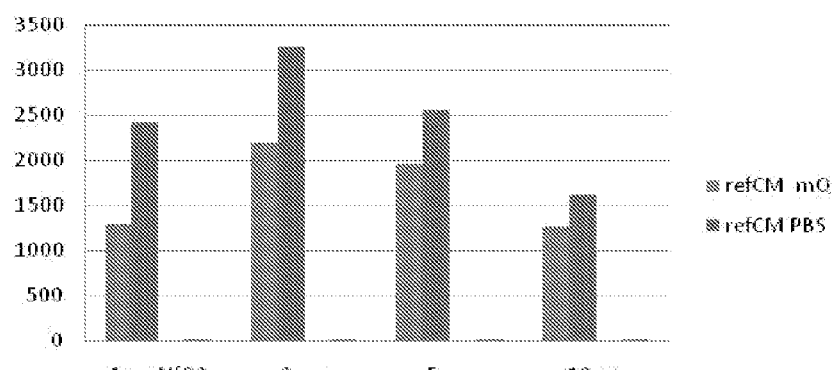
FIGS. 5A and 5B show the fluorescence signals of two different probes on the surface of a wiregrid which were inkjet printed on wiregrids with $HfO_2$ coating at different thicknesses, as indicated. The difference between the probes is the buffer composition which was used with printing.
Figure 5B:
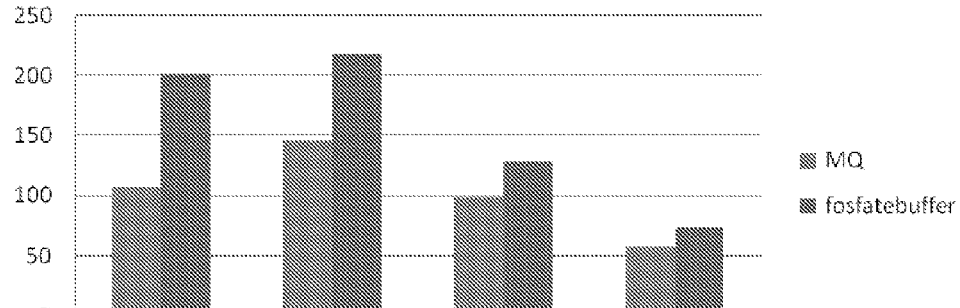
Figure 6:
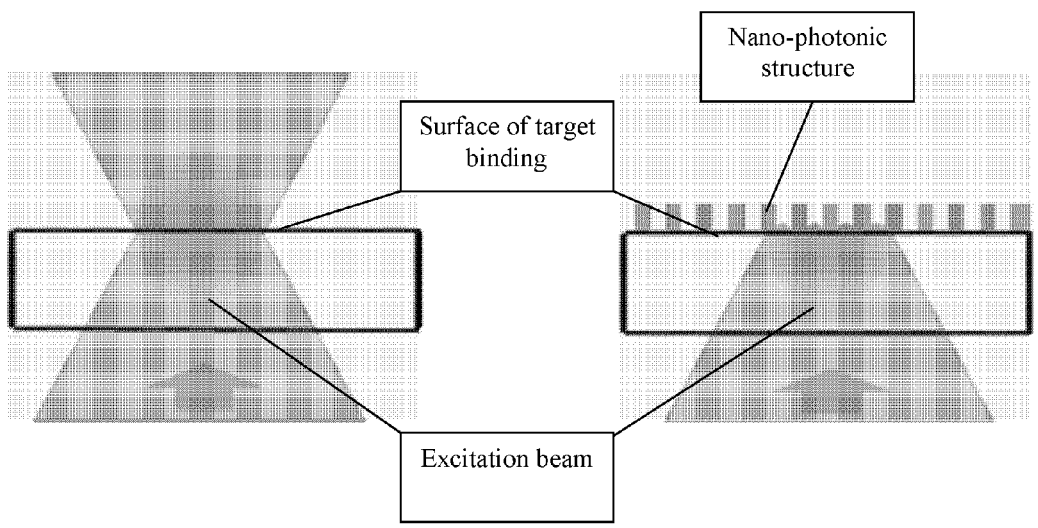
FIG. 6 shows a comparison of optical arrangement without (left) and with (right) nano-photonic structure with a focused excitation beam. The nano-photonic structure confines the excitation light to a small volume between the nano structures.

Using $HfO_2$ as coating it was found that a thickness of 2 nm is optimal for obtaining the highest signal and highest signal to background from a wiregrid biosensor. Two different probes were inkjet printed on wiregrids with $HfO_2$ coating at different thicknesses, i.e. at 1 nm, 2 nm, 5 nm, and 10 nm. For the printing different buffer compositions were used (MQ buffer and PBS or phosphate buffer). As can be derived from FIGS. 5A and 5B a thickness of 2 nm provided optimal results under the tested conditions, i.e. the highest signals and the highest signal to background ratio. These devices showed no increase in background signal even after immersion in 5×SSC with 0.1% SDS for several days.

The invention claimed is:

1. A device comprising:
   an electrode for measuring dielectric properties of a surrounding medium, the electrode including:
   a nano-structure made of an electrically conductive material; and
   a barrier coating including an oxide of Ti, Zr, Hf, Nb, Ta, Mo, Sc, Y, Ge, La, Ce, Pr, Nd, Sm, Eu, Gd, Dy, Ho, Er, Tm, Yb, Lu, Sr, Al, B, Ba, Bi, and/or Mg deposited in a thickness of at least 1 nm by atomic layer deposition (ALD) on said nano-structure and a chemical function configured to couple chemically with biomolecules;
   wherein said nano-structure is a nano-photonic structure and wherein said device allows for surface specific detection by creation of an evanescent field in the apertures of said nano-photonic structure; and
   wherein said nano-structure includes a wiregrid of wires or fibers.

2. The device of claim 1, wherein said device comprises nano-scale apertures with dimensions of less than the optical resolution of light in at least one direction.

3. The device of claim 1, wherein said device is a sequencing device, a fluorescence detector, or a microarray for the detection of nucleic acids or proteins.

4. The device of claim 1, wherein the nano-structure includes Al and the barrier coating includes Hf oxide.

5. The device of claim 4, wherein the barrier coating has a thickness between 1 and 12 nm.

6. The device of claim 1, wherein the barrier layer has a thickness of 1-2 nm.

7. The device of claim 1, further including a plastic carrier which supports the nano-structure.

8. The device of claim 1, wherein the barrier coating has one thickness on one portion of the nanostructure and a different thickness on another portion of the nano-structure.

9. The device of claim 1, wherein the chemical function includes one or more of aldehydes, primary amines, secondary amines, carboxy groups, and epoxides.

10. The device of claim 1, wherein only portions of the barrier coating include the chemical function.

11. The device of claim 1, wherein the wires or fibers are in a range of 50-150 nm in thickness.

12. The device of claim 1, wherein the wires or fibers are in a range of 10-50 nm in evanescent decay length between wires.

13. The device of claim 1, further including a biomolecule coupled with the chemical function.

14. A method of detecting a target compound in a device as defined in claim 1, comprising the steps of:

(a) emitting a beam or radiation having a wavelength incident at said device;
(b) providing, by said device, evanescent radiation, in response to the radiation incident at said device; and
(c) detecting emitted radiation from said target compound present in said device in response to said incident radiation.

15. A bioassay device having an electrode comprising:
a nano-photonic structure configured for surface specific detection by creation of an evanescent field in nano-scale apertures of the nano-photonic structure, wherein said nano-photonic structure is made of electrically conductive material including Al; and
an atomic layer deposition (ALD) deposited barrier coating including Hf oxide coating the nano-structure with a thickness of 1-2 nm; and
wherein said nano-photonic structure covered by the barrier coating is part of a wire grid including a plurality of wires or fibers.

16. The bioassay device of claim 15, further comprising one or more chemical functions configured to chemically couple to biomolecules.

17. A bioassay device having an electrode comprising:
a nano-photonic structure configured for surface specific detection by creation of an evanescent field in nano-scale apertures of the nano-photonic structure, wherein said nano-photonic structure is made of electrically conductive material including Al; and
an atomic layer deposition (ALD) deposited barrier coating including Hf oxide coating the nano-structure with a thickness of 1-2 nm; and
wherein said nano-photonic structure covered by the barrier coating is part of a wire grid including a plurality of wires or fibers; and
wherein the nano-structure includes apertures of a first type with a first in-plane dimension below a defraction limit and a second in-plane dimension above the defraction limit.

18. A bioassay device having an electrode comprising:
a nano-photonic structure configured for surface specific detection by creation of an evanescent field in nano-scale apertures of the nano-photonic structure, wherein said nano-photonic structure is made of electrically conductive material including Al; and
an atomic layer deposition (ALD) deposited barrier coating including Hf oxide coating the nano-structure with a thickness of 1-2 nm; and
wherein said nano-photonic structure covered by the barrier coating is part of a wire grid including a plurality of wires or fibers; and
wherein the electrode further includes an optical waveguide which supports the barrier coated nanostructure, the waveguide including a transparent substrate and a transparent core layer.

* * * * *